(12) United States Patent
Vaska et al.

(10) Patent No.: US 6,237,605 B1
(45) Date of Patent: May 29, 2001

(54) METHODS OF EPICARDIAL ABLATION

(75) Inventors: Matthias Vaska, Menlo Park; Daniel D. Merrick, Pleasanton; Ajit S. Shah, Portola Valley; Casper deClerq, San Francisco, all of CA (US)

(73) Assignee: Epicor, Inc., Menlo Park, CA (US)

( * ) Notice: Subject to any disclaimer, the term of this patent is extended or adjusted under 35 U.S.C. 154(b) by 0 days.

(21) Appl. No.: 09/157,824

(22) Filed: Sep. 21, 1998

Related U.S. Application Data

(63) Continuation-in-part of application No. 08/943,683, filed on Oct. 15, 1997, now Pat. No. 6,161,543, which is a continuation-in-part of application No. 08/735,036, filed on Oct. 22, 1996, now abandoned.

(51) Int. Cl.[7] .................................................. A61B 19/00
(52) U.S. Cl. .............................. 128/898; 606/41; 607/122
(58) Field of Search .............................. 128/898; 606/41; 607/101, 116, 122; 600/374

(56) References Cited

U.S. PATENT DOCUMENTS

| | | |
|---|---|---|
| 3,862,627 | 1/1975 | Hans, Sr. . |
| 4,736,749 | 4/1988 | Lundback . |

(List continued on next page.)

FOREIGN PATENT DOCUMENTS

| | | |
|---|---|---|
| 2 094 636 | 9/1982 | (GB) . |
| 2 289 510A | 11/1995 | (GB) . |
| WO 95/17222 WO | 6/1995 | (WO) . |
| 95/30380A | 11/1995 | (WO) . |

(List continued on next page.)

OTHER PUBLICATIONS

Cox et al., "The Surgical Treatment of Atrial Fibrillation, IV Surgical Technique," *J. Thorac Cardiovasc Surg,* 1991; 101: 584–592.

Wonnell et al., "Evaluation of Microwave and Radio Frequency Catheter Ablation in a Myocardium–Equivalent Phantom Model," *IEEE Transactions on Biomedical Engineering,* 1992;39(10):1086–1095.

(List continued on next page.)

*Primary Examiner*—Michael Peffley
(74) *Attorney, Agent, or Firm*—Jens E. Hoekendijk

(57) ABSTRACT

The invention provides apparatus and methods for mapping conduction pathways and creating transmural lesions in the heart wall for the treatment of atrial fibrillation. The apparatus may include at least one epicardial ablation probe having a plurality of electrodes for creating a transmural lesion. The apparatus and method facilitate the formation of a transmural lesion which electrically isolates the pulmonary veins from the surrounding myocardium without cutting or penetrating the pericardial reflections.

49 Claims, 13 Drawing Sheets

U.S. PATENT DOCUMENTS

| | | |
|---|---|---|
| 4,802,475 | 2/1989 | Weshahy . |
| 4,815,470 | 3/1989 | Curtis et al. . |
| 5,108,390 | 4/1992 | Potocky et al. . |
| 5,147,355 | 9/1992 | Friedman et al. . |
| 5,224,943 | 7/1993 | Goddard . |
| 5,231,995 | 8/1993 | Desai . |
| 5,254,116 | 10/1993 | Baust et al. . |
| 5,263,493 | 11/1993 | Avitall . |
| 5,281,215 | 1/1994 | Milder . |
| 5,295,484 | 3/1994 | Marcus et al. . |
| 5,324,284 | 6/1994 | Imran . |
| 5,334,181 | 8/1994 | Rubinsky et al. . |
| 5,348,554 | 9/1994 | Imran et al. . |
| 5,353,783 | 10/1994 | Nakao et al. . |
| 5,385,148 | 1/1995 | Lesh et al. . |
| 5,405,376 | 4/1995 | Mulier et al. . |
| 5,423,807 | 6/1995 | Milder . |
| 5,423,811 | 6/1995 | Imran et al. . |
| 5,431,649 | 7/1995 | Mulier et al. . |
| 5,433,708 | 7/1995 | Nichols et al. . |
| 5,435,308 | 7/1995 | Gallup et al. . |
| 5,437,651 | 8/1995 | Todd et al. . |
| 5,450,843 | 9/1995 | Moll et al. . |
| 5,465,717 | 11/1995 | Imran et al. . |
| 5,478,330 | 12/1995 | Imran et al. . |
| 5,487,385 | 1/1996 | Avitall . |
| 5,487,757 | 1/1996 | Truckai et al. . |
| 5,520,682 | 5/1996 | Baust et al. . |
| 5,536,267 | 7/1996 | Edwards et al. . |
| 5,545,200 | 8/1996 | West et al. . |
| 5,549,661 | 8/1996 | Kordis et al. . |
| 5,555,883 | 9/1996 | Avitall . |
| 5,560,362 | 10/1996 | Sliwa, Jr. et al. . |
| 5,575,766 | 11/1996 | Swartz et al. . |
| 5,575,810 | 11/1996 | Swanson et al. . |
| 5,578,007 | 11/1996 | Imran . |
| 5,582,609 | 12/1996 | Swanson et al. . |
| 5,607,462 | 3/1997 | Imran . |
| 5,630,837 | 5/1997 | Crowley . |
| 5,643,197 | 7/1997 | Brucker et al. . |
| 5,656,029 | 8/1997 | Imran et al. . |
| 5,658,278 | 8/1997 | Imran et al. . |
| 5,676,662 | 10/1997 | Fleischhacker et al. . |
| 5,676,693 | 10/1997 | LaFontaine . |
| 5,678,550 | 10/1997 | Bassen et al. . |
| 5,680,860 | 10/1997 | Imran . |
| 5,681,278 | 10/1997 | Igo et al. . |
| 5,681,308 | 10/1997 | Edwards et al. . |
| 5,687,723 | 11/1997 | Avitall . |
| 5,687,737 * | 11/1997 | Branham et al. ................... 128/710 |
| 5,690,611 | 11/1997 | Swartz et al. . |
| 5,697,925 | 12/1997 | Taylor . |
| 5,697,927 | 12/1997 | Imran et al. . |
| 5,697,928 * | 12/1997 | Walcott et al. ...................... 606/41 |
| 5,716,389 | 2/1998 | Walinsky et al. . |
| 5,718,241 | 2/1998 | Ben-Haim et al. . |
| 5,718,701 | 2/1998 | Shai et al. . |
| 5,720,775 | 2/1998 | Lanard . |
| 5,730,074 | 3/1998 | Peter . |
| 5,730,127 | 3/1998 | Avitall . |
| 5,730,704 | 3/1998 | Avitall . |
| 5,733,280 | 3/1998 | Avitall . |
| 5,755,760 | 5/1998 | Maguire et al. . |
| 5,769,846 | 6/1998 | Edwards et al. . |
| 5,782,828 * | 7/1998 | Chen et al. ........................ 606/42 |
| 5,792,140 * | 8/1998 | Tu et al. ........................... 606/41 |
| 5,800,428 | 9/1998 | Nelson et al. . |
| 5,800,482 | 9/1998 | Pomeranz et al. . |
| 5,810,802 | 9/1998 | Panescu et al. . |
| 5,827,216 | 10/1998 | Igo et al. . |
| 5,836,947 | 11/1998 | Fleischman et al. . |
| 5,871,523 | 2/1999 | Fleischman et al. . |
| 5,871,525 | 2/1999 | Edwards et al. . |
| 5,879,295 | 3/1999 | Li et al. . |
| 5,879,296 | 3/1999 | Ockuly et al. . |
| 5,882,346 | 3/1999 | Pomeranz et al. . |
| 5,885,278 | 3/1999 | Fleischman . |
| 5,893,848 * | 4/1999 | Negus et al. ....................... 606/41 |
| 5,895,417 | 4/1999 | Pomeranz et al. . |
| 5,897,554 | 4/1999 | Chia et al. . |
| 5,899,899 | 5/1999 | Arless et al. . |
| 5,902,289 | 5/1999 | Swartz et al. . |
| 5,916,214 | 6/1999 | Cosio et al. . |
| 5,921,924 | 7/1999 | Avitall . |
| 5,921,982 | 7/1999 | Lesh et al. . |
| 5,927,284 | 7/1999 | Borst et al. . |
| 5,928,191 | 7/1999 | Houser et al. . |
| 5,931,810 | 8/1999 | Grabek . |
| 5,931,848 | 8/1999 | Saadat . |
| 5,938,659 * | 8/1999 | Tu et al. .............................. 606/41 |
| 5,954,661 | 9/1999 | Greenspon et al. . |
| 5,971,983 | 10/1999 | Lesh . |
| 6,012,457 | 1/2000 | Lesh . |

FOREIGN PATENT DOCUMENTS

| | | |
|---|---|---|
| WO 97/06727 | 2/1997 | (WO) . |
| WO 97/41793 | 11/1997 | (WO) . |
| WO 97/43970 | 11/1997 | (WO) . |
| WO 98/17187 | 4/1998 | (WO) . |
| WO 98/26724 | 6/1998 | (WO) . |
| WQ 98/24488 | 6/1998 | (WO) . |
| WO 98/37822 | 9/1998 | (WO) . |
| WO 98/48881 | 11/1998 | (WO) . |
| WO 98/49957 | 11/1998 | (WO) . |
| WO 99/02096 | 1/1999 | (WO) . |
| WO 99/04696 | 2/1999 | (WO) . |
| WO 99/48421A1 | 9/1999 | (WO) . |
| WO 99/56812 | 11/1999 | (WO) . |
| WO 99/59486 | 11/1999 | (WO) . |

OTHER PUBLICATIONS

He et al., "Preliminary Results Using Ultrasound Energy for Ablation of the Ventricular Myocardium in Dogs," *Am J Card,* 1994;73:1029–1031.

Elvan et al., "Radiofrequency Catheter Ablation of the Atria Eliminates Pacing–Induced Sustained Atrial Fibrillation and Reduces Connexin in 43 Dogs," *Circulation,* 1997;96(5):1675–1685.

He et al., "Application of Ultrasound Energy for Intracardiac Ablation of Arrhythmias," *The European Society of Cardiology,* 1995;16:961–966.

Zimmer et al., "The Feasibility of Using Ultrasound for Cardiac Ablation," *IEEE Transactions on Biomedical Engineering,* 1995;42(9):891–897.

Avitall et al., "A Thoracoscopic to Ablate Atrial Fibrillation Via Linear Radiofrequency Lesion Generation on the Epicardium of Both Atria," PACE, 1996;19(Part II): 626,#241.

Fieguth et al., "Inhibition of Atrial Fibrillation by Pulmonary Vein Isolation and Auricular Resection—Experimental Study in a Sheep Model," *European Journal of Cardio–Thoracic Surgery,* 1997;11:714–721.

Pfeiffer et al., "Epicardial Neodymium . . . ," *Am Heart J,* 1996;94(12):3221–3225.

Hynynen et al., "Cylindrical Ultrasonic Transducers for Cardiac Catheter Ablation," *IEEE Transactions on Biomedical Engineering,* 1997;44(2):144–151.

Elvan et al., "Radiofrequency Catheter Ablation of theAtria Eliminates Pacing–Induced Sustained Atrial Fibrillation and Reduces Connexin 43 in Dogs," *Circulation,* 95:5, Sep. 2, 1997, pp. 1675–1685.

Olgin et al., "Electrophysical Effects of Long. Linear Atrial Lesions Placed Under Intracardiac Ultrasound Guidance," *Circulation,* 1997;96(8):2715–2721.

Weber, "Laser versus Radiofrequency Catheter Ablation of Ventricular Myocardium in Dogs: A Comparative Test," *Cardiology,* 1997: 88:346–352.

Inoue et al., "Video Assisted Thoracoscopic and Cardioscopic Radiofrequency Maze Ablation," *ASAIO Journal,* 1997;43:334–337.

Sosa et al., "Radiofrequency Catheter Ablation of Ventricular Tachycardia Guided by Nonsurgical Epicardial Mapping in Chronic Chagasic heart Disease," *PACE,* Jan. 1999; 22 (Part I), 128–130.

Chevalier, et al., "Thoracoscopic Epicardial Radiofrequency Ablation for Vagal Atrial Fibrillation in Dogs," *PACE* Jun. 1999; 22 (Part I), 880–886.

Cox et al., "The Maze III Procedure for Treatment of Atrial Fibrillation," *Cardiac Arrhythmias,* 78: 460–475.

Stone et al., "Ablation of Atrial Fibrillation by the Maze Procedure," *Surgical Forum, Cardiothoracic Surgery,* date unknown, 213–215.

\* cited by examiner

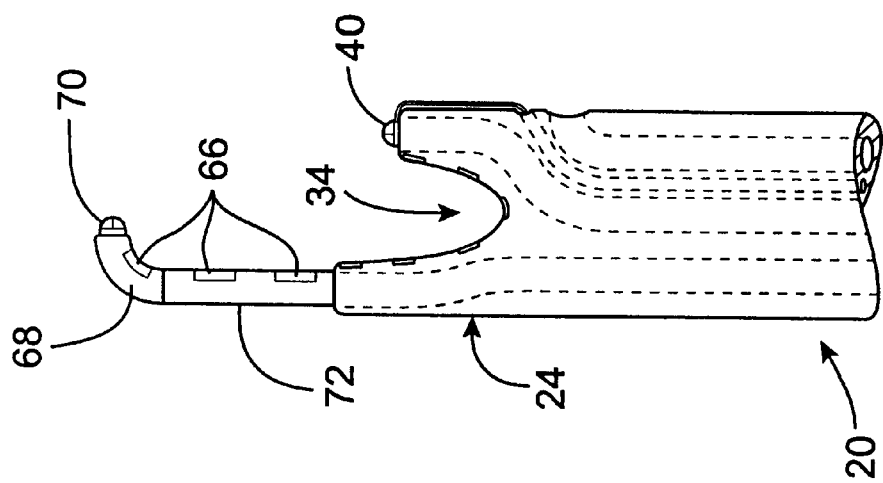
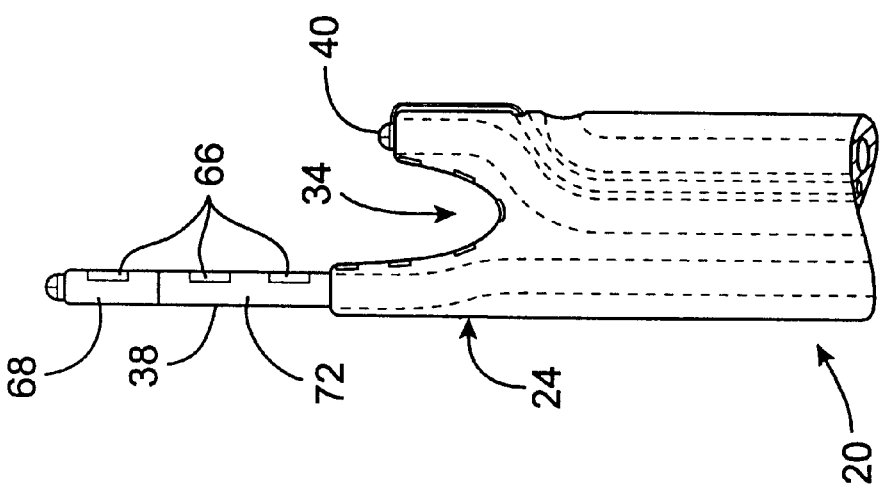
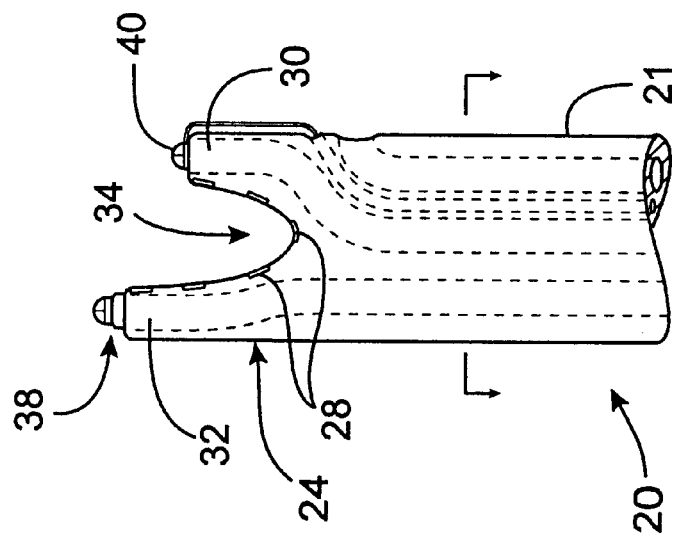
FIG. 2C
FIG. 2B
FIG. 2A

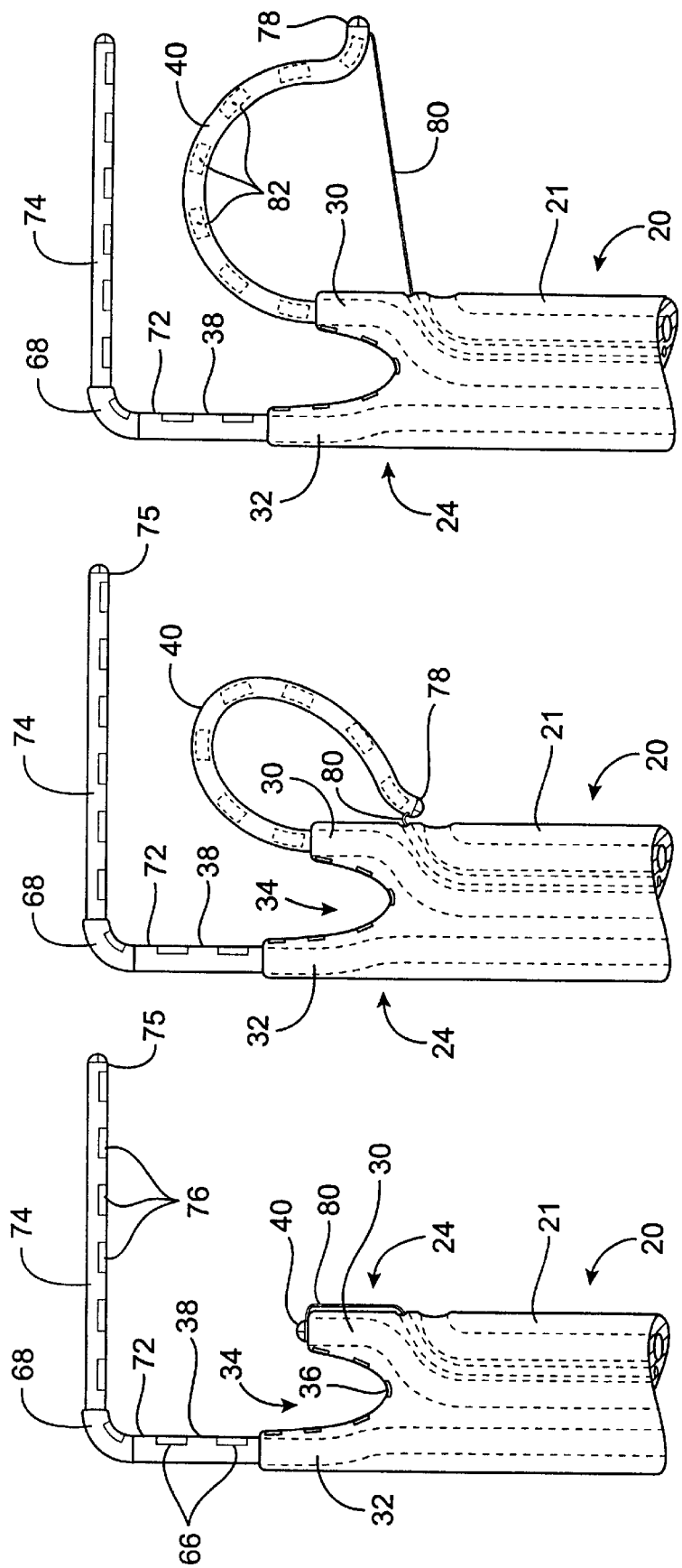

METHODS OF EPICARDIAL ABLATION

CROSS-REFERENCE TO RELATED APPLICATIONS

This application is a continuation-in-part of application Ser. No. 08/943,683, filed Oct. 15, 1997, now U.S. Pat. No. 6,161,543 which is a continuation-in-part of application Ser. No. 08/735,036, filed Oct. 22, 1996, now abandoned, the complete disclosures of which are hereby incorporated herein by reference for all purposes.

FIELD OF THE INVENTION

This invention relates generally to the diagnosis and treatment of electrophysiological diseases of the heart, and more specifically to devices and methods for epicardial mapping and ablation for the treatment of atrial fibrillation.

BACKGROUND OF THE INVENTION

Atrial fibrillation results from disorganized electrical activity in the heart muscle, or myocardium. The surgical maze procedure has been developed for treating atrial fibrillation and involves the creation of a series of surgical incisions through the atrial myocardium in a preselected pattern so as to create conductive corridors of viable tissue bounded by scar tissue. While very effective in treating atrial fibrillation, the maze procedure is highly invasive, high in moribidity and mortality, and difficult to perform by even the most skilled surgeons. The procedure not only requires a median sternotomy or other form of gross thoracotomy for access to the heart, but requires stopping the heart and establishing cardiopulmonary bypass, to which a significant part of the trauma, morbidity and mortality of the maze procedure may be attributed.

As a less invasive alternative to the surgical incisions used in the maze procedure, transmural ablation of the heart wall has been proposed. Such ablation may be performed either from within the chambers of the heart (endocardial ablation) using endovascular devices (e.g. catheters) introduced through arteries or veins, or from outside the heart (epicardial ablation) using devices introduced into the chest through surgical incisions. Various ablation technologies have been proposed, including cryogenic, radiofrequency (RF), laser and microwave. The ablation devices are used to create elongated transmural lesions—that is, lesions extending through a sufficient thickness of the myocardium to block electrical conduction—which form the boundaries of the conductive corridors in the atrial myocardium. Perhaps most advantageous about the use of transmural ablation rather than surgical incisions is the ability to perform the procedure on the beating heart without the use of cardiopulmonary bypass.

In performing the maze procedure and its variants, whether using ablation or surgical incisions, it is generally considered most efficacious to include a transmural incision or lesion that isolates the pulmonary veins from the surrounding myocardium. The pulmonary veins connect the lungs to the left atrium of the heart, and join the left atrial wall on the posterior side of the heart. This location creates significant difficulties for endocardial ablation devices for several reasons. First, while many of the other lesions created in the maze procedure can be created from within the right atrium, the pulmonary venous lesions must be created in the left atrium, requiring either a separate arterial access point or a transeptal puncture from the right atrium. Second, the elongated and flexible endovascular ablation devices are difficult to manipulate into the complex geometries required for forming the pulmonary venous lesions and to maintain in such positions against the wall of the beating heart. This is very time-consuming and can result in lesions which do not completely encircle the pulmonary veins or which contain gaps and discontinuities. Third, visualization of endocardial anatomy and endovascular devices is often inadequate and knowing the precise position of such devices in the heart can be difficult, resulting in misplaced lesions. Fourth, ablation within the blood inside the heart can create thrombus which, in the right chambers, is generally filtered out by the lungs rather than entering the bloodstream. However, on the left side of the heart where the pulmonary venous lesions are formed, thrombus can be carried by the bloodstream into the coronary arteries or the vessels of the head and neck, potentially resulting in myocardial infarction, stroke or other neurologic sequelae. Finally, the heat generated by endocardial devices which flows outward through the myocardium cannot be precisely controlled and can damage extracardiac tissues such as the pericardium, the phrenic nerve and other structures.

If, on the other hand, epicardial ablation devices are utilized to form the pulmonary venous lesions, other challenges are presented. First, the posterior location of the pulmonary veins is extremely difficult to access through thoracic incisions without gross manipulations of the heart. Such manipulations are not generally possible if minimally-invasive techniques are being utilized via small thoracic access ports, or if the procedure is being performed on a beating heart without cardiopulmonary bypass. Further complicating epicardial access are the pericardial reflections, where the pericardium attaches to the heart wall near the pulmonary veins. The pericardial reflections are located so as to prohibit positioning a device completely around the pulmonary veins without cutting away or puncturing through the reflections. Such cutting or puncturing of the pericardial reflections is risky and difficult, particularly if working through small incisions in the chest without a clear view and open access to the posterior side of the heart. Furthermore, surgical repair of any damaged tissue is almost impossible without highly invasive open heart surgery.

What are needed, therefore, are devices and methods for forming transmural lesions that islolate the pulmonary veins from the surrounding myocardium which overcome these problems. The devices and methods will preferably be utlized epicardially to avoid the need for access into the left chambers of the heart and to minimize the risk of producing thrombus. The devices and methods should be useful through small access ports in the chest using minimally invasive techniques. The devices and methods will preferably avoid the need for cutting or puncturing the pericardial reflections. The devices and methods should further be useful on the beating heart without requiring the use of cardiopulmonary bypass and should not require significant manipulation or retraction of the heart.

SUMMARY OF THE INVENTION

The present invention meets these and other objectives by providing epicardial ablation devices and methods useful for creating transmural lesions that electrically isolate the pulmonary veins for the treatment of atrial fibrillation. The devices and methods may be utilized through a small access port in the chest, preferably through a subxiphoid penetration, and positioned within the pericardium and around the pulmonary veins without cutting or puncturing the pericardial reflections. Advantageously, the devices and methods do not require the large thoracic incision used in the conventional maze procedure, and may be used on the beating heart without cardiopulmonary bypass. By eliminating the need for ablation within the left atrium, the risk of thrombus formation is minimized. The devices and methods of the invention are more easily visualized, faster to use, and more accurately positionable than known cardiac ablation catheters and devices, enable the formation of continuous, uninterrupted lesions around the pulmonary veins, and protect extracardiac tissues from injury.

In a first embodiment, a method of forming a transmural lesion in a wall of the heart adjacent to the pulmonary veins comprises the steps of placing at least one ablation device through a thoracic incision and through a pericardial penetration so that the at least one ablation device is disposed in contact with an epicardial surface of the heart wall; positioning the at least one ablation device adjacent to the pulmonary veins on a posterior aspect of the heart while leaving the pericardial reflections intact; and transmurally ablating the heart wall with the at least one ablating device to create at least one transmural lesion adjacent to the pulmonary veins. The ablation device is preferably placed through a small puncture, incision, or access port in the chest, either between the ribs or in a subxiphoid position, for minimal trauma, with visualization provided by fluoroscopy, endoscopy, transesophageal echocardiography, or other conventional form of minimally-invasive imaging. While the method may be performed with the heart stopped and circulation supported with cardiopulmonary bypass, the method is preferably performed with the heart beating so as to minimize morbidity, mortality, complexity and cost.

In another aspect of the invention, an apparatus for forming a transmural lesion in the heart wall adjacent to the pulmonary veins comprises, in a preferred embodiment, an elongated flexible shaft having a working end and a control end; an ablation device attached to the working end for creating a transmural lesion in the heart wall; a control mechanism at the control end for manipulating the working end; and a locating device near the working end configured to engage one or more of the pulmonary veins, or a nearby anatomical structure such as a pericardial reflection, for positioning the working end adjacent to the pulmonary veins. The locating device may comprise a catch, branch, notch or other structure at the working end configured to engage one or more of the pulmonary veins or other anatomical structure such as the inferior vena cava, superior vena cava, or one of the pericardial reflections. The ablation device may be a radiofrequency electrode, microwave transmitter, cryogenic element or any of the other known types of ablation devices suitable for forming transmural lesions. Preferably, the apparatus includes a plurality of such ablation devices arranged along the working end in a linear pattern suitable for forming a continuous, uninterrupted lesion around or on the pulmonary veins.

The working end may additionally include one or more movable elements that are manipulated from the control end and which may be moved into a desired position after the working end has been located near the pulmonary veins. Slidable, rotatable, articulated, pivotable, bendable, preshaped or steerable elements may be used. Additional ablation devices may be mounted to these movable elements to facilitate formation of transmural lesions. The movable elements may be deployed to positions around the pulmonary veins to create a continuous transmural lesion which electrically isolates the pulmonary veins from the surrounding myocardium.

In addition, a mechanism may be provided for urging all or part of the working end against the epicardium to ensure adequate contact with the ablation devices. This mechanism may be, for example, one or more suction holes in the working end through which suction may be applied to draw the working end against the epicardium, or an inflatable balloon mounted to the outer side of the working end such that, upon inflation, the balloon engages the inner wall of the pericardium and forces the working end against the epicardium. This also functions to protect extracardiac tissues such as the pericardium from injury by retracting such tissues away from the epicardial region which is being ablated, and, in the case of the balloon, providing an insulated barrier between the electrodes of the ablation probe and the extracardiac tissues.

The apparatus may be either a single integrated device or two or more devices which work in tandem. In either case, the apparatus may have two or more tips at the working end which are positioned on opposing sides of a tissue layer such as a pericardial reflection. A device may be provided for approximating the two free ends on opposing sides of the tissue layer, such as an electromagnet mounted to one or both of the free ends. In this way, a continuous lesion may be created in the myocardium from one side of the pericardial reflection to the other without puncturing or cutting away the pericardial reflection.

The apparatus may further include a working channel through which supplemental devices may be placed to facilitate visualization, tissue manipulation, supplementary ablation, suction, irrigation and the like.

The apparatus and methods of the invention are further useful for mapping conduction pathways in the heart (local electrograms) for the diagnosis of electrophysiological diseases. Any of the electrodes on the apparatus may be individually selected and the voltage may be monitored to determine the location of conduction pathways. Alternatively, the apparatus of the invention may be used for pacing the heart by delivering current through one or more selected electrodes at levels sufficient to stimulate heart contractions.

Additionally, although the ablation apparatus and methods of the invention are preferably configured for epicardial use, the principles of the invention are equally applicable to endocardial ablation catheters and devices. For example, an endocardial ablation apparatus according to the invention would include a locating device configured to engage an anatomical structure accessible from within the chambers of the heart such as the coronary sinus (from the right atrium), pulmonary artery (from the right ventricle), or the pulmonary veins (from the left atrium), and the ablation device would be positionable in a predetermined location relative to the locating device. The endocardial apparatus could further include suction holes, expandable balloons, or other mechanisms for maintaining contact between the ablation device and the interior surface of the heart wall.

Other aspects and advantages of the invention are disclosed in the following detailed description and in the accompanying drawings.

BRIEF DESCRIPTION OF THE DRAWINGS

FIGS. 2A–2F are side views of a working end of the left ablation probe of FIG. 1A in various configurations thereof.

DETAILED DESCRIPTION OF SPECIFIC EMBODIMENTS

Figure 1A:
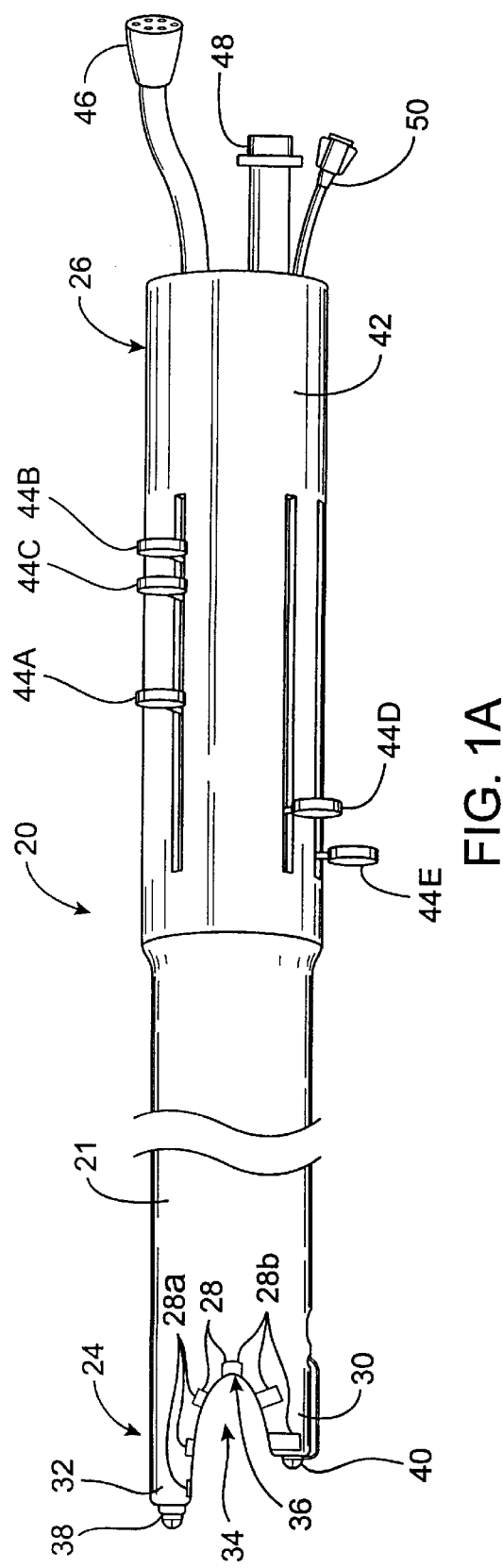
FIG. 1A is side view of a left ablation probe according to the invention.
Figure 1B:
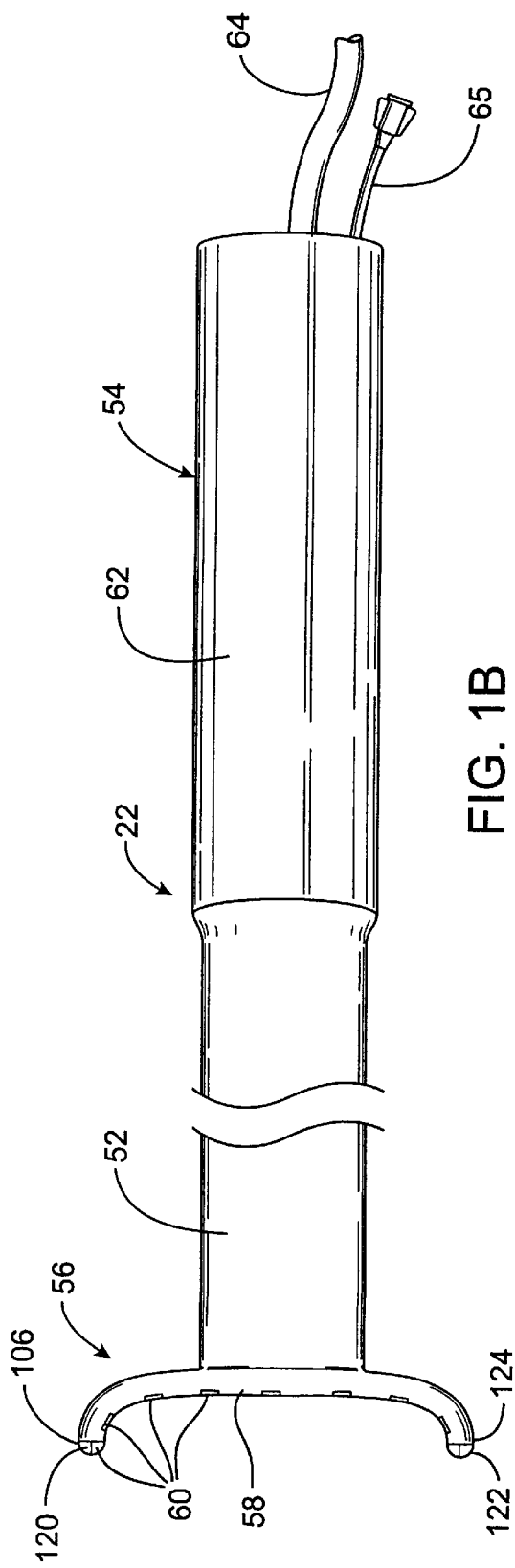
FIG. 1B is a side view of a right ablation probe according to the invention.

FIGS. 1A–1B illustrate a first embodiment of the apparatus of the invention. In this embodiment, the apparatus comprises a left ablation probe 20, shown in FIG. 1A, and a right ablation probe 22, shown in FIG. 1B, which work in tandem to form a transmural lesion isolating the pulmonary veins from the surrounding myocardium. Left ablation probe 20 has a flexible shaft 21 extending to a working end 24 configured for insertion into the chest cavity through a small incision, puncture or access port. Opposite working end 24, shaft 21 is attached to a control end 26 used for manipulating the working end 24 from outside the chest. Shaft 21 is dimensioned to allow introduction through a small incision in the chest, preferably in a subxiphoid location, and advanced to the pulmonary veins on the posterior side of the heart. Preferably, shaft 21 is configured to be flexible about a first transverse axis to allow anterior-posterior bending and torsional flexibility, but relatively stiff about a second transverse axis perpendicular to the first transverse axis to provide lateral bending stiffness. In an exemplary embodiment, shaft 21 has a length in the range of about 10–30 cm, and a rectangular cross-section with a width-to-height ratio of about 2–5, the cross-sectional width being about 6–35 mm and the cross-sectional height being about 3–17 mm. Shaft 21 is made of a flexible biocompatible polymer such as polyurethane or silicone, and preferably includes radiopaque markers or a radiopaque filler such as bismuth or barium sulfate.

Working end 24 includes a plurality of electrodes 28 for delivering radiofrequency (RF) current to the myocardium so as to create transmural lesions of sufficient depth to block electrical conduction. Electrodes 28 may be partially-insulated solid metal rings or cylinders, foil strips, wire coils or other suitable construction for producing elongated lesions. Electrodes 28 are spaced apart a distance selected so that the lesions created by adjacent electrodes contact or overlap one another, thereby creating a continuous, uninterrupted lesion in the tissue underlying the electrodes. In an exemplary embodiment, electrodes 28 are about 2–20 mm in length and are spaced apart a range of 1–6 mm. As an alternative to RF electrodes, microwave transmitters, cryogenic elements or other types of ablation devices suitable for forming transmural lesions may be used. Electrodes 28 are positioned so as to facilitate lesion formation on the three-dimensional topography of the left atrium around the left inferior pulmonary vein. For example, lateral electrodes 28a face medially to permit ablation of the myocardium on the lateral side of the left inferior pulmonary vein and medial electrodes 28b face anteriorly to permit ablation of the posterior surface of the myocardium adjacent to the left inferior pulmonary vein.

Working end 24 further includes a locating mechanism which locates the working end at one of the pulmonary veins and helps to maintain it in position once located. In a preferred embodiment, working end 24 is bifurcated into two branches 30, 32, and the locating mechanism is a notch 34 disposed between the two branches. Notch 34 tapers into a concave surface 36 so as to receive one of the pulmonary veins between branches 30, 32 and to atraumatically engage the pulmonary vein against concave surface 36. In an exemplary embodiment, notch 34 is about 10 to 30 mm in width at its widest point between branches 30, 32 and tapers toward concave surface 36 which has a radius of curvature of about 4 to 15 mm, so as to conform to the outer curvature of the pulmonary vein. Preferably, notch 34 is sized and positioned for placement against the left inferior pulmonary vein, as described more fully below. Alternatively, the locating mechanism may be configured to engage another anatomic structure such as the inferior vena cava, superior vena cava, pericardial reflections, pulmonary vein, aorta, pulmonary artery, atrial appendage, or other structure in the space between the pericardium and the myocardium.

Working end 24 further includes a superior sub-probe 38 and an inferior sub-probe 40 which are slidably extendable from working end 24, as further described below.

Control end 26 includes a handle 42 and a plurality of slidable actuators 44A–44E, which are used to extend superior sub-probe 38 and inferior sub-probe 40 from working end 24, and to perform other functions as described below. An electrical connector 46 suitable for connection to an RF generator is mounted to handle 42 and is electrically coupled to electrodes 28 at working end 24. Also mounted to handle 42 are a working port 48 in communication with a working channel 92, described below, and a connector 50 for connection to a source of inflation fluid or suction, used for purposes described below.

Right ablation probe 22 has a flexible shaft 52 extending from a control end 54 to a working end 56. Working end 56 has a cross-member 58 to which are mounted a plurality of electrodes 60. Cross member 58 preferably has tips 59 which are pre-shaped or deflectable into a curve so as to conform to the right lateral walls of the right pulmonary veins, and which are separated by a distance selected so that the two right pulmonary veins may be positioned between them, usually a distance of about 20–50 mm. Electrodes 60 are sized and positioned so as to create a continuous lesion along the right side (from the patient's perspective) of the pulmonary veins as described more fully below. In an exemplary embodiment, electrodes 60 are about 2–20 mm in length, and are spaced apart about 1–6 mm. Shaft 52 is dimensioned to allow introduction through a small incision in the chest, preferably in a subxiphoid location, and advanced to the pulmonary veins on the posterior side of the heart. Shaft 52 will have dimensions, geometry and materials like those of shaft 21 of left ablation probe 20, described above.

Control end 54 includes a handle 62. An electrical connector 64 adapted for connection to an RF generator is attached to handle 62 and is electrically coupled to electrodes 60 at working end 56. An inflation or suction connector 65 is mounted to handle 62 and adapted for connection to a source of inflation fluid or suction, for purposed described below. Handle 62 may further include a working port (not shown) like working port 48 described above in connection with left ablation probe 20.

FIGS. 2A–2E illustrate the deployment of the various components of working end 24 of left ablation probe 20. Superior sub-probe 38 is slidably extendable from working end 24 as shown in FIG. 2B. A plurality of electrodes 66 are mounted to superior sub-probe 38 and are sized and positioned to create a continuous lesion along the left side of the pulmonary veins. Superior sub-probe 38 has an articulated or steerable section 68 which can be selectively shaped into the position shown in FIG. 2C, with its distal tip 70 pointing in a lateral direction relative to the more straight proximal portion 72.

As shown in FIG. 2D, an inner probe 74 is slidably extendable from superior sub-probe 38 and is directed by steerable section 68 in a lateral direction opposite notch 34. Inner probe 74 is separated from notch 34 by a distance selected such that inner probe 74 may be positioned along the superior side of the pulmonary veins when the left inferior pulmonary vein is positioned in notch 34. In an exemplary embodiment, the maximum distance from concave surface 36 to inner probe 74 is about 20–50 mm. A plurality of electrodes 76 are mounted to inner probe 74 and positioned to enable the creation of a continuous transmural lesion along the superior side of the pulmonary veins as described more fully below.

Referring to FIG. 2E, inferior sub-probe 40 is slidably extendable from working end 24. Its distal tip 78 is attached to a tether 80 extending through a lumen in shaft 21. Tether 80 may be selectively tensioned to draw distal tip 78 away from inner probe 74 (toward control end 26), imparting a curvature to inferior sub-probe 40. Inferior sub-probe 40 is constructed of a resilient, bendable plastic which is biased into a straight configuration. When inferior sub-probe 40 has been advanced sufficiently, tether 80 may be released, whereby the resiliency of inferior sub-probe 40 causes it to conform to the pericardial reflection and the medial and/or inferior sides of the four pulmonary veins. Inferior sub-probe 40 further includes a plurality of electrodes 82 sized and positioned to produce a continuous transmural lesion in the myocardium along the inferior side of the pulmonary veins, as described more fully below.

Figure 3:
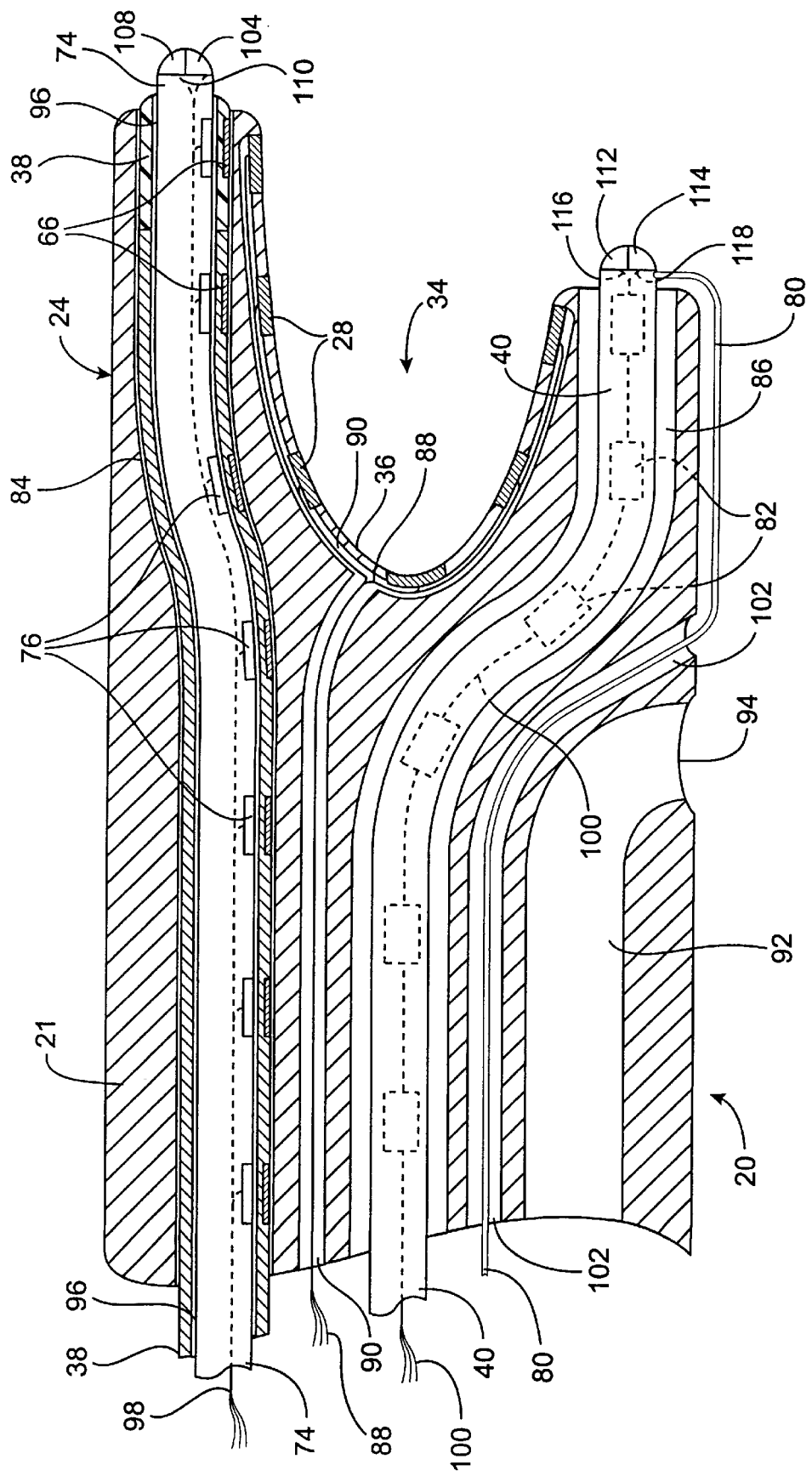
FIG. 3 is a side cross-section of the working end of the left ablation probe of FIG. 1A.
Figure 4:
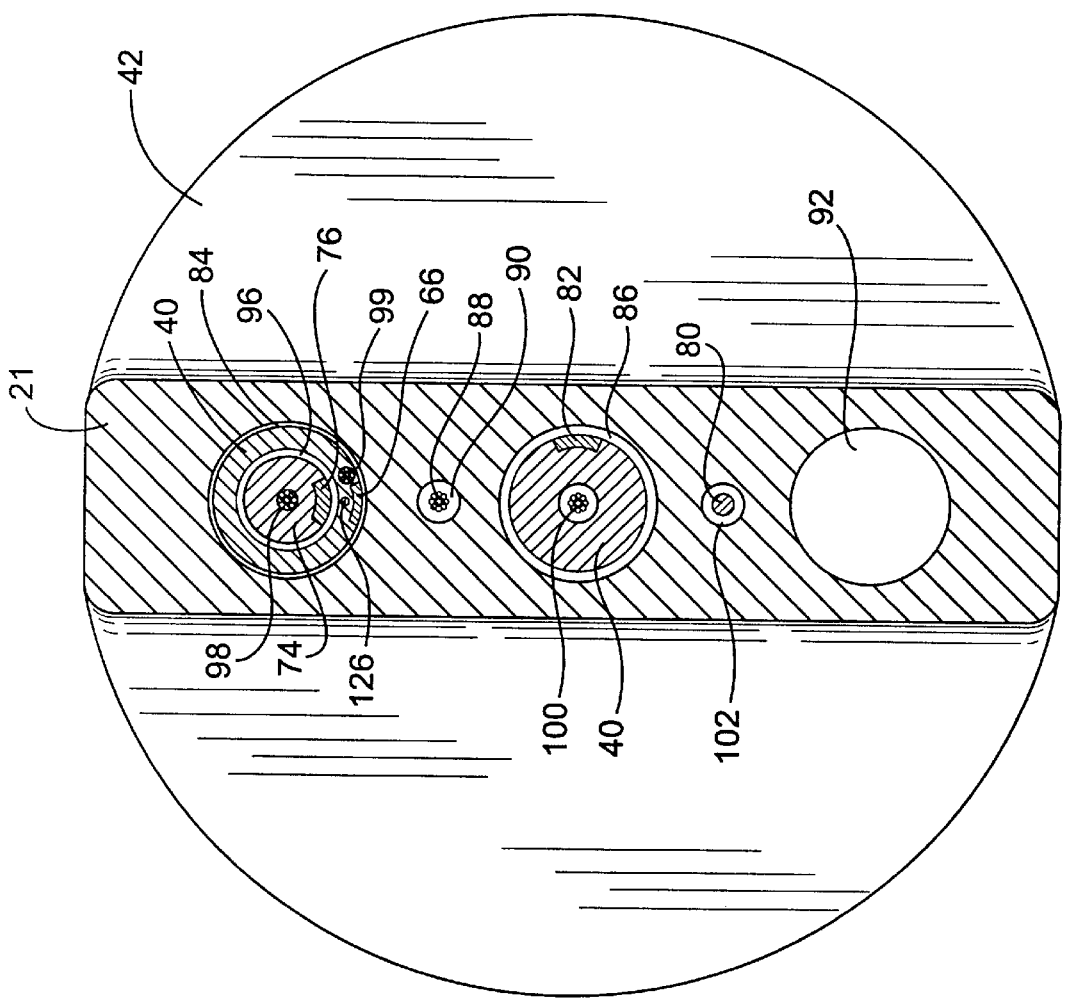
FIG. 4 is a transverse cross-section of the shaft of the left ablation probe of FIG. 1A.

Referring to FIGS. 3 and 4, superior sub-probe 38 is slidably disposed in a first lumen 84 and inferior sub-probe 40 is slidably disposed in a second lumen 86 in shaft 21. Electrodes 28 along notch 34 are coupled to wires 88 disposed in a wire channel 90 running beneath electrodes 28 and extending through shaft 21. Each electrode is coupled to a separate wire to allow any electrode or combination of electrodes to be selectively activated. Shaft 21 also includes a working channel 92 extending to an opening 94 in working end 24 through which instruments such as endoscopes, suction/irrigation devices, mapping and ablation devices, tissue retraction devices, temperature probes and the like may be inserted. Superior sub-probe 38 has an inner lumen 96 in which inner probe 74 is slidably disposed. Electrodes 76 on inner probe 74 are coupled to wires 98 extending through inner probe 74 to connector 46 on handle 42, shown in FIG. 1A. Similarly, electrodes 66 on superior sub-probe 38 are coupled to wires 99 (FIG. 4) and electrodes 82 on inferior sub-probe 40 are coupled to wires 100, both sets of wires extending to connector 46 on handle 42. Tether 80 slidably extends through tether lumen 102 in shaft 21.

The distal end of inner probe 74 has a tip electrode 104 for extending the transmural lesion produced by electrodes 76. Preferably, inner probe 74 further includes a device for approximating the tip of inner probe 74 with the superior tip 106 of right ablation probe 22 (FIG. 1B) when the two are separated by a pericardial reflection. In a preferred embodiment, a first electromagnet 108 is mounted to the distal end of inner probe 74 adjacent to tip electrode 104. First electromagnet 108 is coupled to a wire 110 extending to handle 42, where it is coupled to a power source and a switch (not shown) via connector 46 or a separate connector. Similarly, a second electromagnet 112 is mounted to distal tip 78 of inferior sub-probe 40, adjacent to a tip electrode 114, which are coupled to wires 116, 118 extending to a connector on handle 42. As shown in FIG. 1B, a third electromagnet 120 is mounted to superior tip 106 of right ablation probe 22, and a fourth electromagnet 122 is mounted to inferior tip 124 of right ablation probe 22. Electromagnets 120, 122 are coupled to wires (not shown) extending to a connector on handle 62 for coupling to a power source and switch. In this way, superior tip 106 and inferior tip 124 may be approximated with inner probe 74 and inferior sub-probe 40 across a pericardial reflection by activating electromagnets 108, 112, 120, 122.

It should be noted that thermocouples, thermistors or other temperature monitoring devices may be mounted to the working ends of either left or right ablation probes 20, 22 to facilitate temperature measurement of the epicardium during ablation. The thermocouples may be mounted adjacent to any of the electrodes described above, or may be welded or bonded to the electrodes themselves. The thermocouples will be coupled to wires which extend through shafts 21, 52 alongside the electrode wires to connectors 46, 64 or to separate connectors on handles 42, 62, facilitating connection to a temperature monitoring device.

Figures 5A, 5B, 5C:
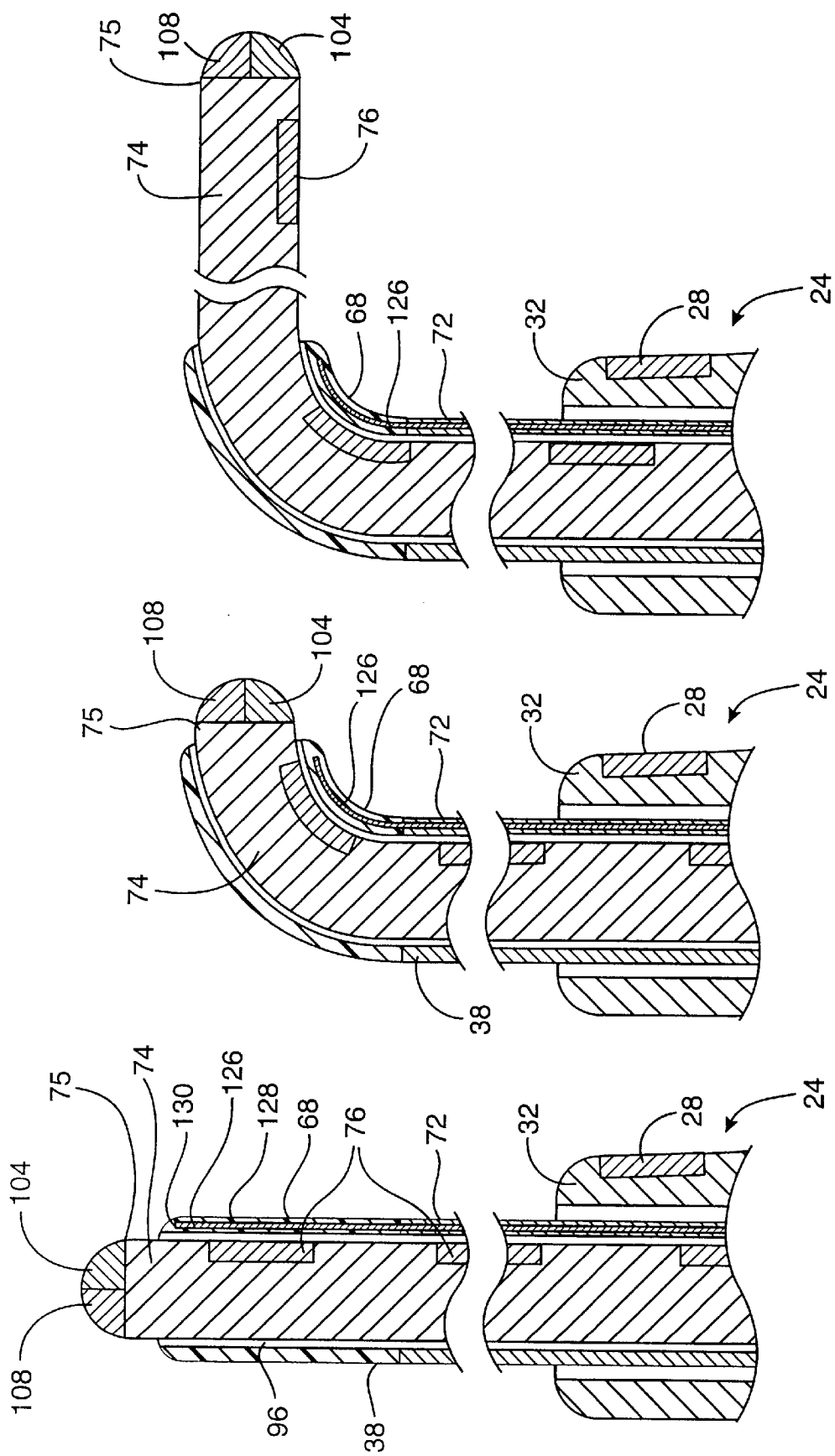
FIGS. 5A–C are partial side cross-sections of the working end of the left ablation probe of FIG. 1A, showing the deployment of a superior sub-probe and inner probe thereof.

FIGS. 5A–5C illustrate the operation of superior sub-probe 38. Superior sub-probe 38 has a pull wire 126 movably disposed in a wire channel 128 in a sidewall adjacent to inner lumen 96. Pull wire 126 is fixed at its distal end 130 to steerable section 68 of superior sub-probe 38. Steerable section 68 is constructed of a flexible, resilient plastic such that by tensioning pull wire 126, steerable section 68 may be deformed into a curved shape to direct inner probe 74 in a transverse direction relative to the straight proximal portion 72, as shown in FIG. 5B. Once in this curved configuration, inner probe 74 may be slidably advanced from superior sub-probe 38 as shown in FIG. 5C.

Figure 6:
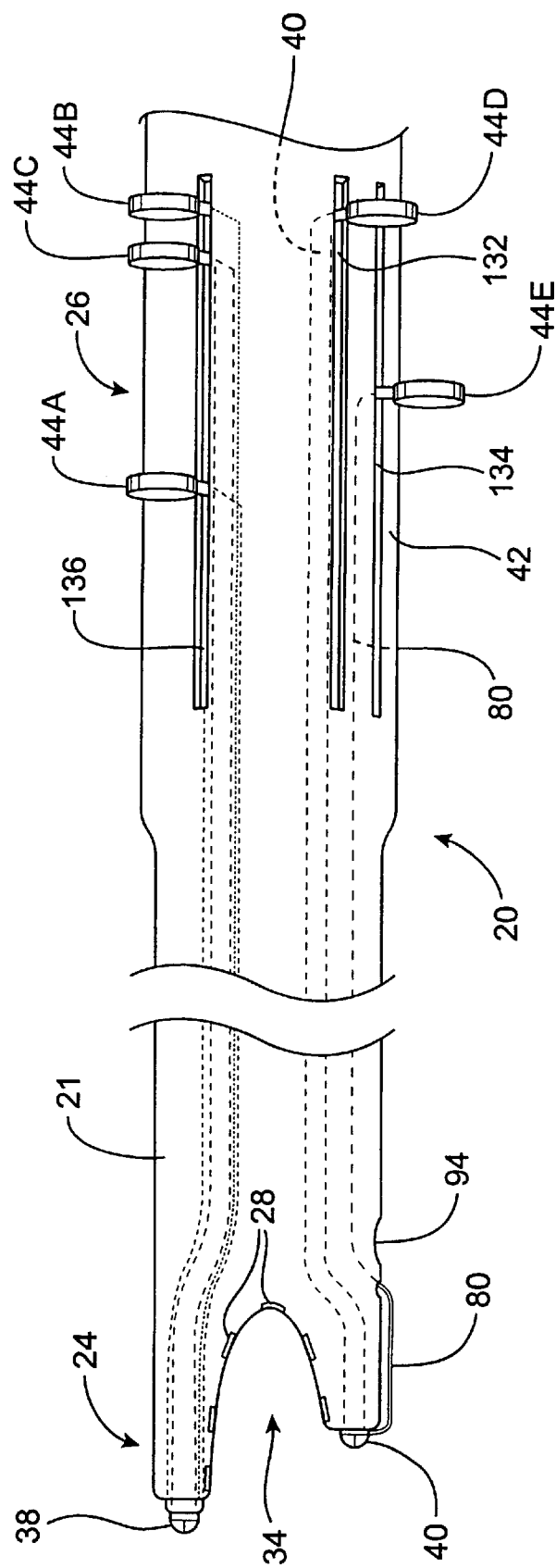
FIG. 6 is a side view of the left ablation probe of FIG. 1A.

Referring to FIG. 6, actuator 44D is slidably disposed in a longitudinal slot 132 in handle 42 and is coupled to the proximal end of inferior sub-probe 40. Actuator 44E is slidably disposed in a longitudinal slot 134 in handle 42 and is coupled to the proximal end of tether 80. When sub-probe 40 is to be deployed, actuator 44D is slid forward, advancing inferior sub-probe 40 distally. Actuator 44E may be allowed to slide forward as well, or it may be held in position to maintain tension on tether 80, thereby bending sub-probe 40 into the curved shape shown in FIG. 2E. When sub-probe 40 has been fully advanced, actuator 44E may be released, allowing distal end 78 of sub-probe 40 to engage the pericardial reflection along the inferior surfaces of the pulmonary veins, as further described below.

Figure 7:
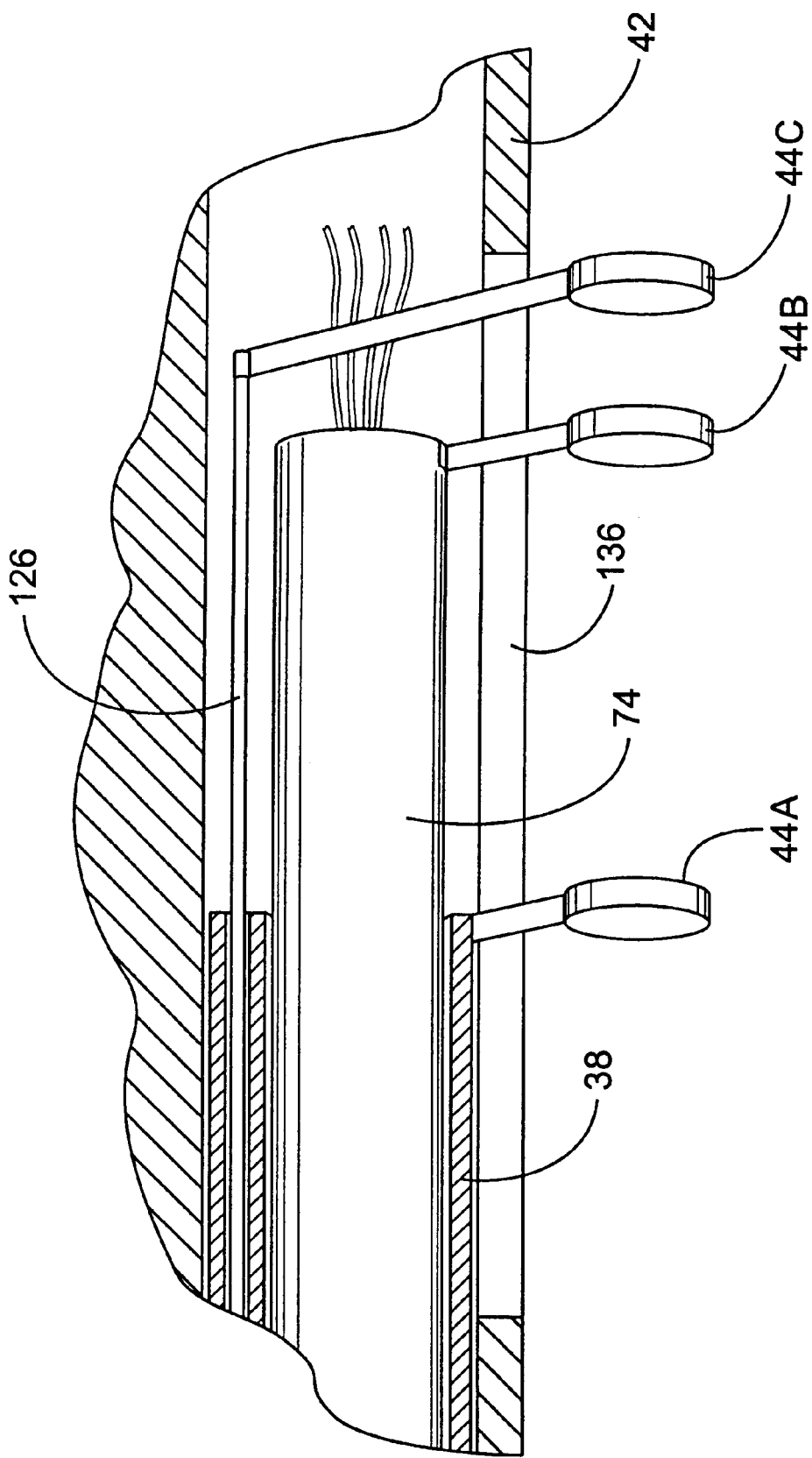
FIG. 7 is a partial side cross-section of the handle of the left ablation probe of FIG. 1A.

Actuators 44A–C are slidably disposed in a longitudinal slot 136 in handle 42, as more clearly shown in FIG. 7. Actuator 44A is attached to the proximal end of superior sub-probe 38, and may be advanced forward to deploy the sub-probe from working end 24, as shown in FIG. 2A. Actuator 44B is attached to inner probe 74, which is frictionally retained in inner lumen 96 such that it is drawn forward with superior sub-probe 38. Actuator 44C is attached to pull wire 126 which is also drawn forward with superior sub-probe 38. In order to deflect the steerable section 68 of superior sub-probe 38, actuator 44C is drawn proximally, tensioning pull wire 126 and bending steerable section 68 into the configuration of FIG. 2C. Finally, to deploy inner probe 74, actuator 44B is pushed forward relative to actuators 44A and 44C, advancing inner probe 74 from superior sub-probe 38 as shown in FIG. 2D.

Referring now to FIGS. 8–11, a preferred embodiment of the method of the invention will be described. Initially, left ablation probe 20 and right ablation probe 22 are connected to an RF generator 140. RF generator 140 will preferably provide up to 150 watts of power at about 500 kHz, and will have capability for both temperature monitoring and impedance monitoring. A suitable generator would be, for example, a Model No. EPT-1000 available from the EP Technologies Division of Boston Scientific Corp. of Natick, Mass. Retraction, visualization, temperature monitoring, suction, irrigation, mapping or ablation devices may be inserted through working port 142. Left ablation probe 20 may further be connected to a source of suction or inflation fluid 144, for reasons described below. If electromagnets are provided on left and right ablation probes 20, 22 as described above, an additional connection may be made to a power supply and switch for operating the electromagnets, or power may be supplied by RF generator 140 through connectors 46, 64.

Figure 9:
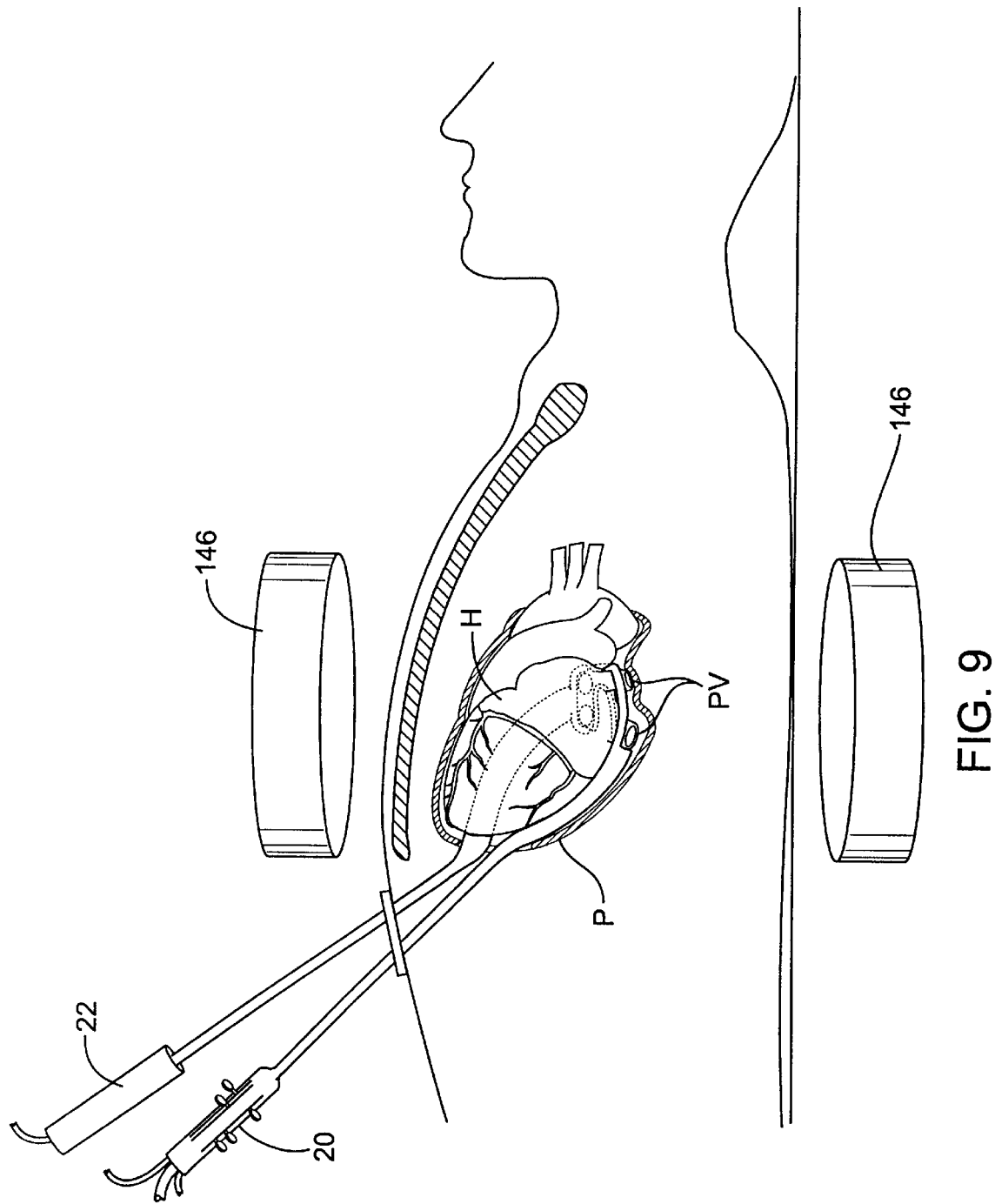
FIG. 9 is a side view of the interior of a patient's thorax illustrating the positioning of the left and right ablation probes according to the method of the invention.

A subxiphoid incision (inferior to the xiphoid process of the sternum) is made about 2–5 cm in length. Under direct vision through such incision or by visualization with an endoscope, a second small incision is made in the pericardium P (FIG. 9). Left ablation probe 20 is introduced through these two incisions and advanced around the inferior wall of the heart H to its posterior side under fluoroscopic guidance using fluoroscope 146. Alternative methods of visualization include echocardiography, endoscopy, transillumination, and magnetic resonance imaging. Left ablation probe 20 is positioned such that left inferior pulmonary vein LI is disposed in notch 34 as shown in the posterior view of the heart in FIG. 10.

Superior sub-probe 38 is then advanced distally from working end 24 until its steerable section 68 is beyond the superior side of the left superior pulmonary vein LS. Steerable section 68 is then deflected into the curved configuration shown in FIG. 10 such that its distal end 70 is superior to the left superior pulmonary vein LS and pointing rightward toward the right superior pulmonary vein RS. Inner probe 74 is then advanced toward the right until its distal tip is very close to or contacting the pericardial reflection PR superior to the right superior pulmonary vein RS.

Inferior sub-probe 40 is next advanced from working end 24 while maintaining tension on tether 80 such that the inferior sub-probe engages and conforms to the shape of the pericardial reflection PR between the left inferior and right inferior pulmonary veins. When inferior sub-probe 40 has been fully advanced, tension is released on tether 80 so that distal tip 78 moves superiorly into engagement with the right inferior pulmonary vein RI adjacent to pericardial reflection PR inferior thereto.

Figure 8:
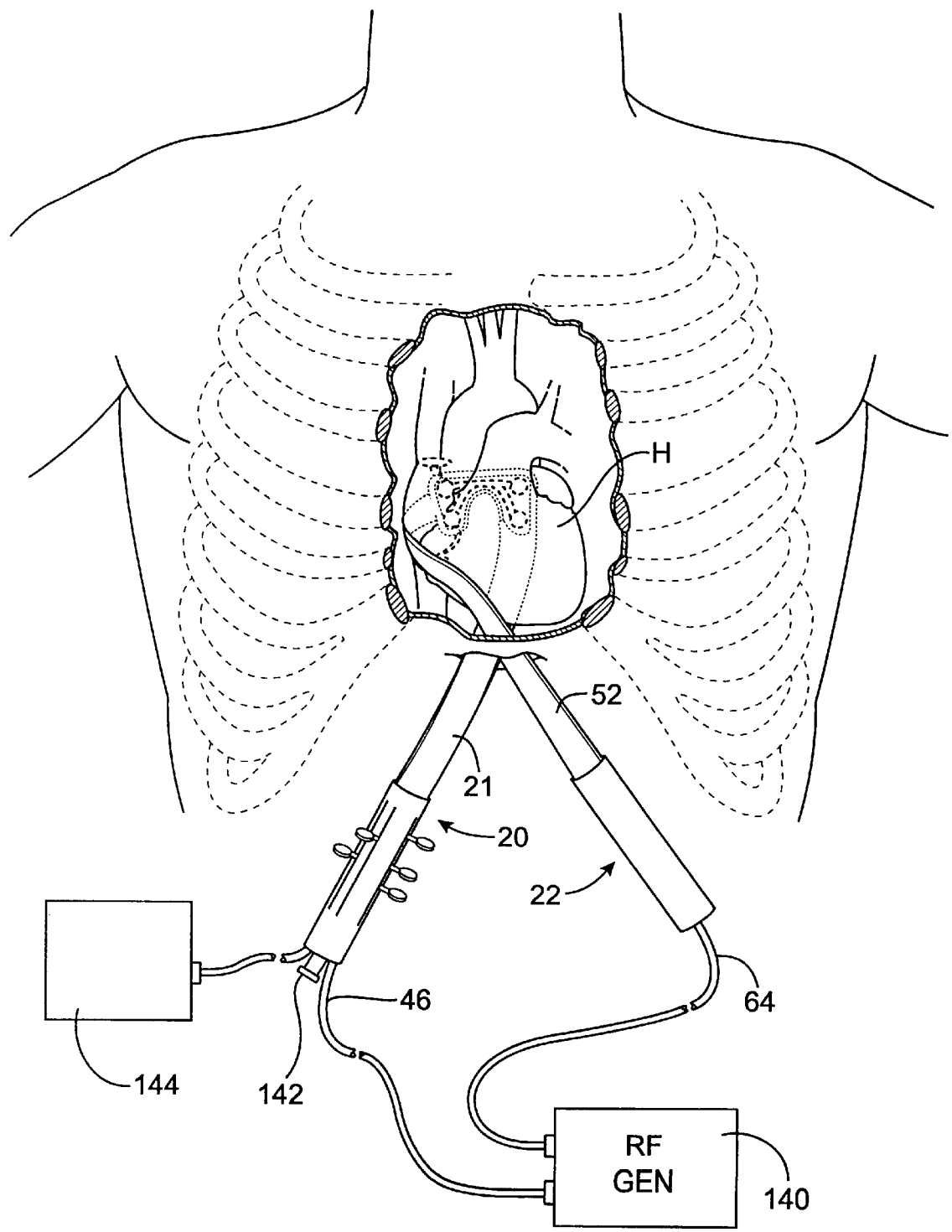
FIG. 8 is an anterior view of the thorax of a patient illustrating the positioning of the left and right ablation probes according to the method of the invention.
Figure 10:
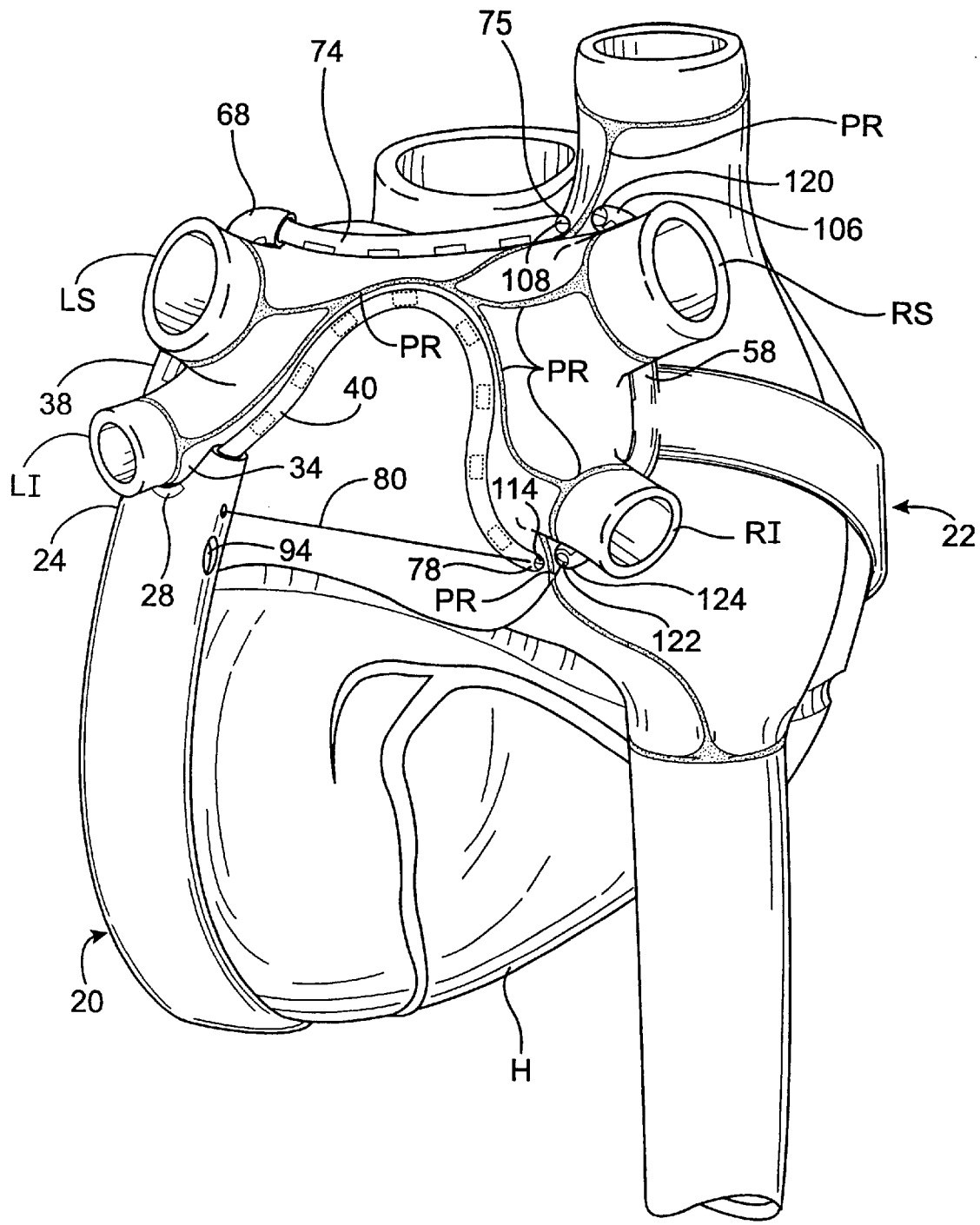
FIG. 10 is a posterior view of a patient's heart illustrating the use of the left and right ablation probes according to the method of the invention.

Right ablation probe 22 is placed through the subxiphoid incision and pericardial incision and advanced around the right side of the heart as shown in FIG. 8. Under fluoroscopic guidance, right ablation probe 22 is positioned such that cross-member 58 engages the right superior and inferior pulmonary veins, as shown in FIG. 10. In this position, superior tip 106 and inferior tip 124 should be generally in opposition to distal tip 75 of inner probe 74 and distal tip 78 of inferior sub-probe 40, respectively, separated by pericardial reflections PR. In order to ensure close approximation of the two tip pairs, electromagnets 108, 120, 114, 122 may be energized, thereby attracting the tips to each other across the pericardial reflections RS.

Figure 11:
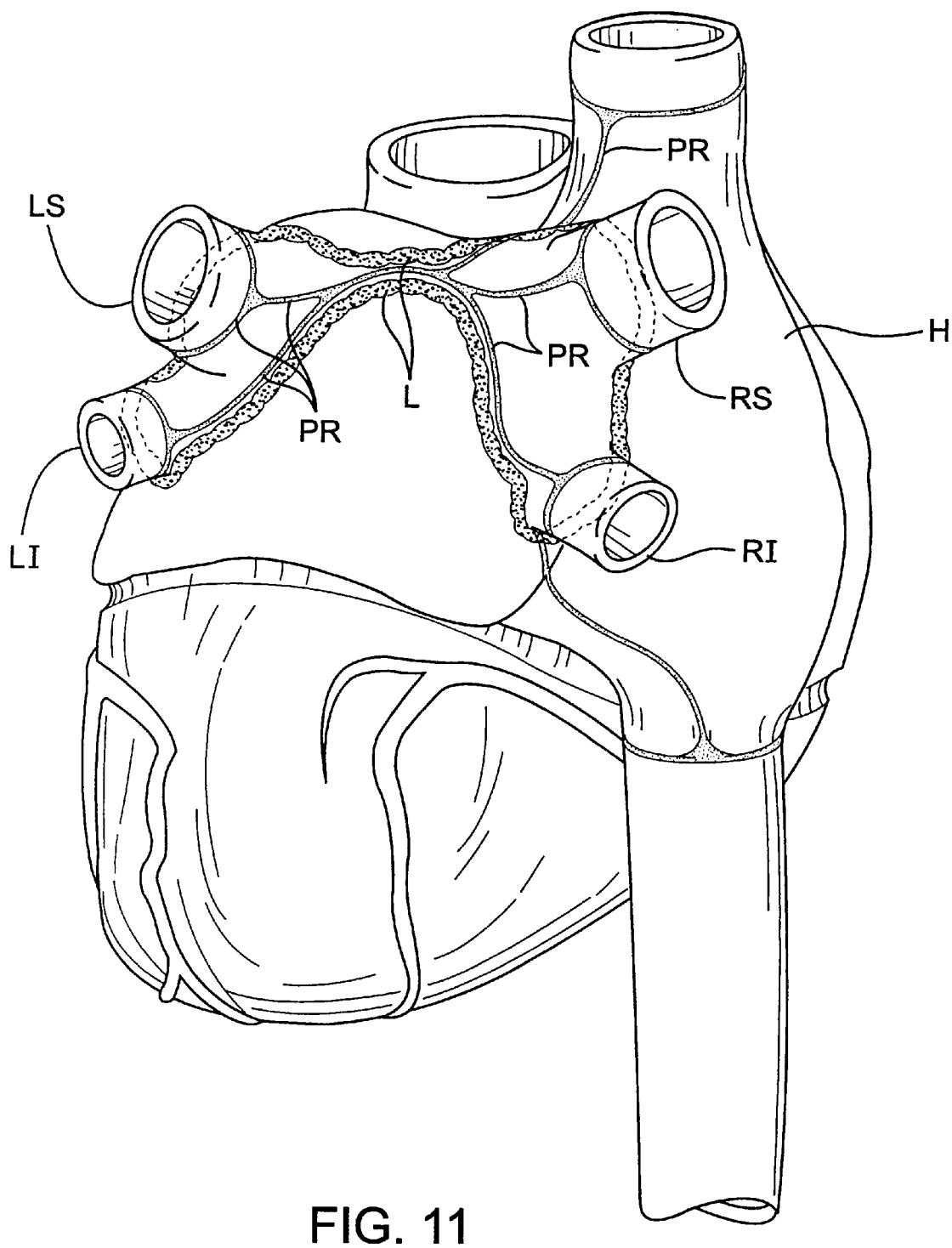
FIG. 11 is a posterior view of a patient's heart illustrating a transmural lesion formed according to the method of the invention.

It should be noted that the pericardium P attaches to the heart at the pericardial reflections PR shown in FIGS. 10–11. Because of the posterior location of the pulmonary veins and the limited access and visualization available, cutting or puncturing the pericardial reflections in the vicinity of the pulmonary veins poses a risk of serious injury to the heart or pulmonary veins themselves. The apparatus and method of the present invention avoid this risk by allowing the pericardial reflections to remain intact, without any cutting or puncturing thereof.

RF generator 140 is then activated to deliver RF energy to electrodes 28, 60, 66, 76, 82, 104, and 112 on left and right ablation probes 20, 22, producing the transmural lesion L shown in FIG. 11. Preferably, power in the range of 20–150 watts is delivered at a frequency of about 500 kHz for a duration of about 30–180 seconds, resulting in localized myocardial temperatures in the range of 45–95° C. Ultrasound visualization may be used to detect the length, location and/or depth of the lesion created. Lesion L forms a continuous electrically-insulated boundary encircling the pulmonary veins thereby electrically isolating the pulmonary veins from the myocardium outside of lesion L.

Ablation probes 20, 22 may further be used for mapping conduction pathways in the heart (local electrocardiograms) for the diagnosis of electrophysiological abnormalities. This is accomplished by selecting any of the electrodes on the ablation probes and monitoring the voltage. A commercially available electrophysiology monitoring system is utilized, which can select any electrode on the ablation probes and monitor the voltage. Various electrodes and various locations on the heart wall may be selected to develop a map of potential conduction pathways in the heart wall. If ablation treatment is then required, the steps outlined above may be performed to create transmural lesions at the desired epicardial locations.

During any of the preceding steps, devices may be placed through working port 142 and working channel 92 to assist and supplement the procedure. For example, a flexible endoscope may be introduced for visualization to assist positioning. Ultrasound probes may be introduced to enhance visualization and for measuring the location and/or depth of transmural lesions. Suction or irrigation devices may be introduced to clear the field and remove fluid and debris. Tissue manipulation and retraction devices may be introduced to move and hold tissue out of the way. Cardiac mapping and ablation devices may also be introduced to identify conduction pathways and to supplement the ablation performed by left and right ablation probes 20, 22.

Furthermore, mapping and ablation catheters, temperature monitoring catheters, and other endovascular devices may be used in conjunction with the left and right ablation probes of the invention by introducing such devices into the right atrium or left atrium either through the arterial system or through the venous system via the right atrium and a transseptal puncture. For example, an ablation catheter may be introduced into the left atrium to ablate any region of the myocardium not sufficiently ablated by left and right ablation probes 20, 22 in order to ensure complete isolation of the pulmonary veins. Additionally, ablation catheters may be introduced into the right chambers of the heart, or epicardial ablation devices may be introduced through incisions in the chest, to create other transmural lesions.

Figure 12:
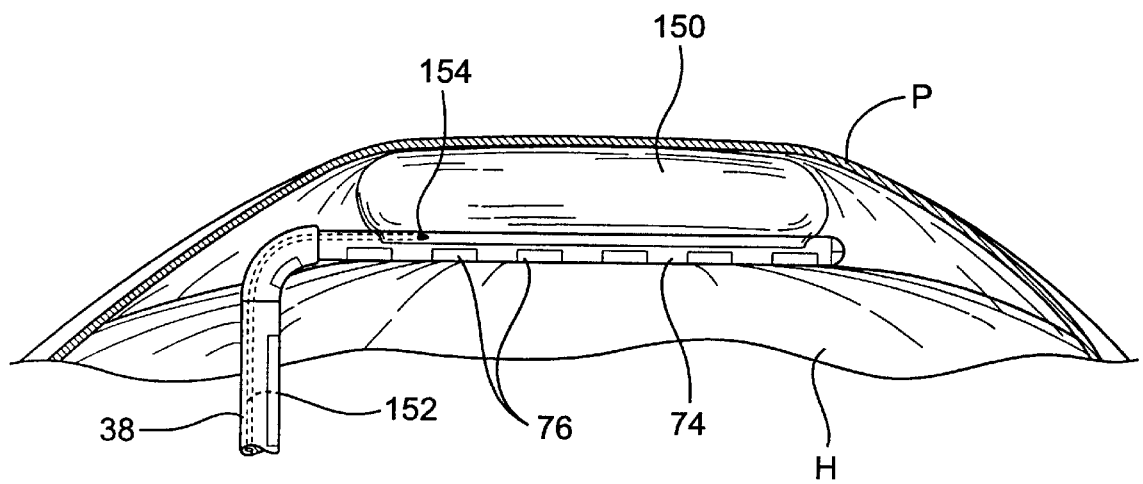
FIGS. 12 and 13 are side views of the left ablation probe of the invention positioned on a patient's heart, showing a balloon and suction ports, respectively, on the inner probe.

In some cases, it may be desirable to actively ensure adequate contact between the epicardium and the electrodes of left and right ablation probes 20, 22. For this purpose, left ablation probe 20 and/or right ablation probe 22 may include one or more expandable devices such as balloons which are inflated in the space between the heart and the pericardium to urge the ablation probe against the epicardial surface. An exemplary embodiment is shown in FIG. 12, in which a balloon 150 is mounted to the outer surface of inner probe 74 opposite electrodes 76 on left ablation probe 20. Inner probe 74 further includes an inflation lumen 152 in communication with an opening 154 within balloon 150 and extending proximally to inflation fitting 50 on handle 42, through which an inflation fluid such as liquid saline or gaseous carbon-dioxide may be delivered. When inflated, balloon 150 engages the inner surface of the pericardium P and urges inner probe 74 against the epicardial surface of heart H. This ensures close contact between electrodes 76 and the epicardium, and protects extracardiac tissue such as the pericardium and phrenic nerve from injury caused by the ablation probes. Balloons or other expandable devices may similarly be mounted to superior sub-probe 38, inferior sub-probe 40, or right ablation probe 22 to ensure sufficient contact between the epicardium and the electrodes on those components.

Figure 13:
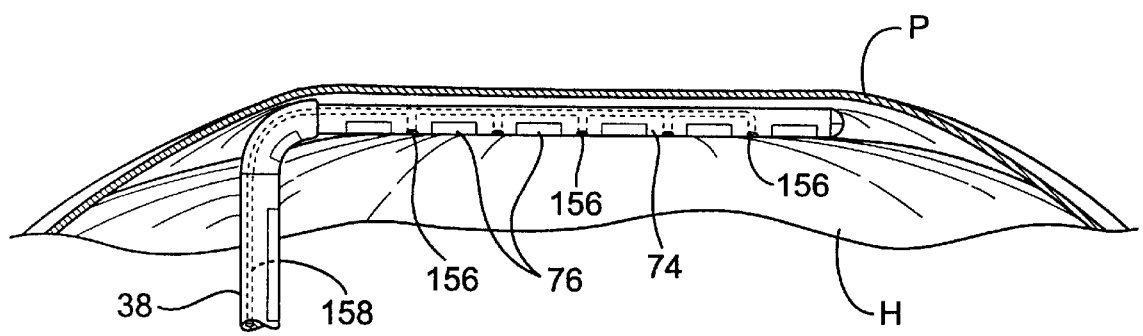

Alternatively or additionally, suction ports may be provided in the ablation probes of the invention to draw the electrodes against the epicardium, as shown in FIG. 13. In an exemplary embodiment, suction ports 156 are disposed in inner probe 74 between or adjacent to electrodes 76. Suction ports 156 are in communication with a suction lumen 158 which extends proximally to suction fitting 48 on handle 42. In this way, when suction is applied through suction port 156, inner probe 74 is drawn tightly against the heart, ensuring good contact between electrodes 76 and the epicardium. In a similar manner, superior sub-probe 38, inferior sub-probe 40 and right ablation probe 22 may include suction ports adjacent to the electrodes on those components to enhance contact with the epicardium.

While the above is a complete description of the preferred embodiments of the invention, various alternatives, substitutions and modifications may be made without departing from the scope thereof, which is defined by the following claims.

What is claimed is:

1. A method of forming a lesion in a wall of the heart, the heart being surrounded by a pericardium, the method comprising:
   providing a first ablation device and a second ablation device each having at least one ablating element, the first ablation device passing through the second ablation device and being slidably received by the second ablation device:
   placing the first and second ablation devices through a thoracic incision and through a pericardial penetration so that the first and second ablation devices are disposed in contact with an epicardial surface of the heart wall; and
   ablating the heart wall to create at least one lesion with the ablating elements of the first and second ablation devices positioned at the epicardial surface of the heart wall.

2. The method of claim 1 wherein the at least one lesion formed by the first and second ablation devices extends continuously to form an elongate lesion.

3. The method of claim 1 wherein the at least one lesion extends continuously around four of the pulmonary veins.

4. The method of claim 1 wherein the at least one lesion electrically isolates the pulmonary veins from a portion of the heart wall.

5. The method of claim 1 wherein the first ablation device has a catch device, and the step of positioning comprises engaging the locating device with at least one of a pulmonary vein, vena cava, aorta, pulmonary artery, atrial appendage, or pericardial reflection.

6. The method of claim 1 wherein at least one of the first and second ablation devices has at least one electrode mounted thereto and the step of ablating comprises applying energy to the heart wall through said electrode.

7. The method of claim 1 wherein the at least one of the first and second ablation devices has a plurality of ablating elements and the step of ablating comprises applying energy to the heart wall through said plurality of ablating elements to create a substantially continuous lesion therebetween.

8. The method of claim 1 wherein the thoracic incision is in a subxiphoid position.

9. The method of claim 1 further comprising viewing the heart using a technique selected from fluoroscopy, echocardiography, endoscopy, transillumination and magnetic resonance imaging during at least one of the steps of placing, positioning and ablating.

10. The method of claim 1 further comprising urging at least one of the first and second ablation devices against the epicardial surface.

11. The method of claim 1 wherein the step of positioning comprises shaping a distal end of the ablation device in a preselected shape.

12. The method of claim 11 wherein the step of shaping comprises moving a steering mechanism coupled to the distal end.

13. The method of claim 12 wherein the step of moving comprises tensioning a wire coupled to the distal end.

14. A method of forming a transmural lesion in a wall of the heart adjacent to or on the pulmonary veins, the heart being surrounded by a pericardium, the method comprising:
   placing at least one ablation device through a thoracic incision and through a pericardial penetration so that the at least one ablation device is disposed in contact with an epicardial surface of the heart wall;
   positioning the at least one ablation device adjacent to the pulmonary veins on a posterior aspect of the heart while leaving the pericardial reflections intact;
   ablating the heart wall to create a lesion around the pulmonary veins with at least one ablation device positioned at the epicardial surface of the heart wall; and
   urging the ablation device against the epicardial surface, wherein the step of urging comprises applying suction through at least one suction port in the ablation device.

15. A method of forming a transmural lesion in a wall of the heart adjacent to or on the pulmonary veins, the heart being surrounded by a pericardium, the method comprising:
   placing at least one ablation device through a thoracic incision and through a pericardial penetration so that the at least one ablation device is disposed in contact with an epicardial surface of the heart wall;
   positioning the at least one ablation device adjacent to the pulmonary veins on a posterior aspect of the heart while leaving the pericardial reflections intact; and ablating the heart wall to create a lesion around the pulmonary veins with at least one ablation device positioned at the epicardial surface of the heart wall; and expanding an expandable member on the ablation device between the pericardium and the epicardium, the expandable member being configured to engage the pericardium to urge the ablation device toward the epicardium.

16. A method of forming a transmural lesion in a wall of the heart adjacent to or on the pulmonary veins, the heart being surrounded by a pericardium, the method comprising:

placing at least one ablation device through a thoracic incision and through a pericardial penetration so that the at least one ablation device is disposed in contact with an epicardial surface of the heart wall;

positioning the at least one ablation device adjacent to the pulmonary veins on a posterior aspect of the heart while leaving the pericardial reflections intact;

ablating the heart wall to create a lesion around the pulmonary veins with at least one ablation device positioned at the epicardial surface of the heart wall; and retracting extracardiac tissue away from the ablation device during the step of ablating.

17. The method of claim 16 wherein the step of retracting comprises expanding and expandable member on the ablation device, the expandable member engaging and retracting the extracardiac tissue away from the ablation device.

18. A method of forming a transmural lesion in a wall of the heart adjacent to or on the pulmonary veins, the heart being surrounded by a pericardium, the method comprising:

placing at least one ablation device through a thoracic incision and through a pericardial penetration so that the at least one ablation device is disposed in contact with an epicardial surface of the heart wall, wherein the at least one ablation device comprises first and second free ends;

positioning the at least one ablation device adjacent to the pulmonary veins on a posterior aspect of the heart while leaving the pericardial reflections intact;

ablating the heart wall to create a lesion around the pulmonary veins with at least one ablation device positioned at the epicardial surface of the heart wall; and positioning the first and second free ends on opposite sides of a tissue layer and approximating the first and second free ends in opposing alignment separated by the tissue layer.

19. The method of claim 18 wherein the step of approximating comprises magnetically attracting the first free end to the second free end.

20. A method of forming a lesion in a wall of the heart, the heart being surrounded by a pericardium, the method comprising:

providing a first ablating device having an ablating element and at least one suction port, the at least one suction port being coupled to a source of vacuum;

placing the first ablation device through a thoracic incision and through a pericardial penetration so that the first ablation device is disposed in contact with an epicardial surface of the heart wall;

ablating the heart wall with the first ablating device to create an elongate continuous lesion in the heart wall with the first ablation device positioned at the epicardial surface of the heart wall; and applying suction through the at least one suction port in the ablation device to urge the ablating device into contact with the epicardial surface of the heart wall.

21. The method of claim 20, wherein:

the placing step is carried out with the first ablating device having a plurality of ablating elements which are spaced apart from one another.

22. The method of claim 21, wherein:

the ablating step is carried out to create an elongate continuous lesion.

23. The method of claim 22, wherein:

the ablating step is carried out to create a closed loop.

24. The method of claim 23, wherein:

the ablating step is carried out to create an elongate continuous lesion around the pulmonary veins.

25. The method of claim 20, wherein:

the ablating step is carried out with the first ablating device having a curved shape to conform to the epicardial surface heart.

26. The method of claim 20, wherein:

the positioning step is carried out with the device having means for locating the device at an anatomical structure.

27. The method of claim 26, wherein:

the positioning step is carried out with the locating means positioned at an exterior surface of one of a pulmonary vein, vena cava, aorta, pulmonary artery, atrial appendage, and pericardial reflection.

28. A method of forming a lesion in a wall of the heart, the heart being surrounded by a pericardium, the method comprising:

providing a first ablation device having an expandable member;

placing the first ablation device through a thoracic incision and through a pericardial penetration so that the first ablation device is disposed in contact with a location on an epicardial surface of the heart wall;

ablating the heart wall to create a lesion with the first ablation device positioned at the epicardial surface of the heart wall; and expanding the expandable member on the first ablation device to hold the first ablation device at the location on the epicardial surface of the heart wall.

29. The method of claim 28, wherein:

the expanding step is carried out to retract extracardiac tissue away from the first ablation device during the step of ablating.

30. The method of claim 28, further comprising the step of:

applying suction through the at least one suction port in the first ablation device to urge the first ablation device into contact with the epicardial surface of the heart wall.

31. The method of claim 28, wherein:

the placing step is carried out with the first ablating device having a plurality of ablating elements which are spaced apart from one another.

32. The method of claim 28, wherein:

the ablating step is carried out to create an elongate continuous lesion.

33. The method of claim 32, wherein:

the ablating step is carried out to create a closed loop.

34. The method of claim 33, wherein:

the ablating step is carried out to create an elongate continuous lesion around the pulmonary veins.

35. The method of claim 28, wherein:

the ablating step is carried out with the first ablating device having a curved shape to conform to the epicardial surface heart.

36. The method of claim 28, wherein:

the positioning step is carried out with the device having means for locating the device at an anatomical structure.

37. The method of claim 36, wherein:

the positioning step is carried out with the locating means positioned at an exterior surface of one of a pulmonary vein, vena cava, aorta, pulmonary artery, atrial appendage, and pericardial reflection.

38. A method of forming a lesion in a wall of the heart, the heart being surrounded by a pericardium, the method comprising:

placing at least one ablation device through a thoracic incision and through a pericardial penetration so that the at least one ablation device is disposed in contact with an epicardial surface of the heart wall, wherein the at least one ablation device has a first end and a second free end;

positioning the at least one ablation device at an epicardial location while leaving a pericardial reflection intact;

ablating the heart wall to create a lesion at the epicardial location of the heart wall; and positioning the first and second free ends on opposite sides of the pericardial reflection and approximating the first and second free ends in opposing alignment separated by the pericardial reflection.

39. The method of claim 38, wherein:

the ablating step is carried out with the at least one ablation device ablating tissue beneath the pericardial reflection while leaving the pericardial reflection intact.

40. The method of claim 38, wherein:

the providing step is carried out with the at least one ablating device comprising a first ablating device and a second ablating device, the first ablating device having the first end and the second ablating element having the second end.

41. The method of claim 38, wherein:

the positioning step is carried out by magnetically attracting the first free end to the second free end.

42. The method of claim 38, further comprising the step of:

applying suction through at least one suction port to urge the at least one ablating device into contact with an epicardial surface.

43. The method of claim 38, wherein:

the placing step is carried out with the at least one ablating device having a plurality of ablating elements which are spaced apart from one another.

44. The method of claim 43, wherein:

the ablating step is carried out to create an elongate continuous lesion.

45. The method of claim 44, wherein:

the ablating step is carried out to create a closed loop.

46. The method of claim 45, wherein:

the ablating step is carried out to create an elongate continuous lesion around the pulmonary veins.

47. The method of claim 38, wherein:

the ablating step is carried out with the at least one ablating device having a curved shape to conform to an epicardial surface.

48. The method of claim 38, wherein:

the positioning step is carried out with the at least one ablating device having means for locating the at least one ablating device at an anatomical structure.

49. The method of claim 48, wherein:

the positioning step is carried out with the locating means positioned at an exterior surface of one of a pulmonary vein, vena cava, aorta, pulmonary artery, atrial appendage, and pericardial reflection.

\* \* \* \* \*